United States Patent [19]
Shelokov

[11] Patent Number: 6,039,763
[45] Date of Patent: Mar. 21, 2000

[54] ARTICULATING SPINAL DISC PROSTHESIS

[75] Inventor: Alexis P. Shelokov, Dallas, Tex.

[73] Assignee: Disc Replacement Technologies, Inc., Dallas, Tex.

[21] Appl. No.: 09/179,324

[22] Filed: Oct. 27, 1998

[51] Int. Cl.$^7$ ............... A61F 2/44; A61F 2/30; A61F 2/38
[52] U.S. Cl. ................... 623/17; 623/18; 623/20
[58] Field of Search ................... 623/17, 20, 18

[56] References Cited

U.S. PATENT DOCUMENTS

| | | |
|---|---|---|
| 4,257,129 | 3/1981 | Volz . |
| 4,349,921 | 9/1982 | Kuntz . |
| 4,759,766 | 7/1988 | Buettner-Janz et al. . |
| 4,955,908 | 9/1990 | Frey et al. . |
| 5,258,031 | 11/1993 | Salib et al. . |
| 5,401,269 | 3/1995 | Büttner-Janz et al. . |
| 5,425,773 | 7/1995 | Boyd et al. ............... 623/17 |
| 5,425,777 | 6/1995 | Sarkisian et al. ........... 623/21 X |
| 5,507,816 | 4/1996 | Bullivant ................... 623/17 |
| 5,556,431 | 9/1996 | Büttner-Janz et al. . |
| 5,562,738 | 10/1996 | Boyd et al. . |
| 5,676,701 | 10/1997 | Yuan et al. ................ 623/17 |
| 5,893,889 | 4/1999 | Harrington ................ 623/17 |
| 5,895,428 | 4/1999 | Berry ...................... 623/17 |

*Primary Examiner*—Michael J. Milano
*Assistant Examiner*—Hieu Phan
*Attorney, Agent, or Firm*—Randall C. Brown; Rick Matos; Akin, Gump, Strauss, Hauer & Feld, L.L.P.

[57] ABSTRACT

The artificial spinal disc of the invention is intended to articulate in a manner resembling a human knee articulation. The artificial spinal disc includes two plates each having a planar outer surface and an articulating inner surface. The planar outer surfaces contact adjacent inferior and superior surfaces of two adjacent vertebrae having the spinal disc implanted therebetween. The planar surfaces of the plates are affixed to the adjacent vertebrae. The articulating surfaces of the artificial spinal disc will be generally bimodal-shaped such that a first articulating surface will have two convex shaped articulating portions and the second articulating surface will have two concave shaped articulating portions. The concave and convex shaped portions of the respective plates will be generally complementary. The articulation of the artificial spinal disc will generally resemble that of a human knee.

25 Claims, 5 Drawing Sheets

ARTICULATING SPINAL DISC PROSTHESIS

FIELD OF THE INVENTION

The present invention relates to a prosthetic spinal disc, and more specifically, to a prosthetic spinal disc which articulates in a manner resembling a human knee.

BACKGROUND OF THE INVENTION

Prosthetic intervertebral discs for use in the lumbar spine are a new technology with a short history of clinical use in Europe. They are used as a substitute for chronically injured or ruptured and excised intervertebral disc in the spinal column of the vertebrae for humans. Such devices employ one, two, three or more individual elements having a wide range of constructs including ball and socket joints, gel filled enclosures, spring-biased plates, plate and joint combinations and others. Prosthetic spinal discs have been used and reported about primarily in the lumbar spine.

Known prosthetic spinal discs generally require some form of articulation or inherent flexibility in the device to permit a spine having the device to maintain its natural posture and range of motion as much as possible.

Several patents disclose particular artificial spinal discs comprising two articulating plate members which are affixed to adjacent superior and inferior vertebrae in one fashion or another. Particular modes of articulation of the two plates has generally been used to distinguish the various devices in this field. As vertebrae generally have rounded outer periphery as viewed from a superior to inferior direction, the outer periphery of known artificial spinal discs are generally rounded, circular, oval, or kidney-shaped. Known artificial discs have also been made from a large variety of materials such as plastic, rubber, metal, ceramic and alloys.

Prosthetic spinal discs comprising two plates, each plate having a planar surface attached to an adjacent vertebra, are disclosed in U.S. Pat. Nos. 4,309,777, 4,759,769 and 5,458,642. Prosthetic spinal discs comprising two plates, each plate having a planar first surface attached to an adjacent vertebra and a contoured opposing second surface separated by an interposed core or member that articulates or cooperates with the contoured surfaces of the respective plates, are disclosed in U.S. Pat. Nos. 4,759,766, 5,314,477, 5,556,431 and 5,562,738.

U.S. Pat. No. 5,401,269 to Büttner-Janz et al. discloses an intervertebral disc endoprosthesis generally comprising at least two articulating plates which are rotatable relative to one another about a vertical axis.

U.S. Pat. No. 4,349,921 to Kuntz discloses an intervertebral disc prosthesis comprising a body having a superior surface, an inferior surface, opposing lateral surfaces and opposing anterior and posterior ends, wherein each of the superior and inferior surfaces is "substantially flat in the lateral-lateral direction over the entirety of the surfaces" and "in the anterior-posterior direction corresponding generally with the shape of a vertebral surface adjacent the disc." The intervertebral disc prosthesis further comprises "means for holding the prosthesis" to a vertebra.

U.S. Pat. No. 5,258,031 to Salib et al. discloses an intervertebral disc arthroplasty comprising: 1) a first member having a first joint surface, a first anterior end and an opposing first posterior end, the anterior and posterior ends defining a transverse midline therebetween; 2) a second member having a second joint surface, a second anterior end and an opposing second posterior end; and 3) a ball and socket joint located between the first and second joint surfaces and between the transverse midline and the first posterior end. The ball and socket joints permits relative rotation of the first and second member about a first axis parallel to the transverse midline and about a second axis perpendicular to the first axis.

U.S. Pat. No. 5,425,773 to Boyd et al. discloses an intervertebral disc arthroplasty comprising: 1) a first member having a first joint surface, a first anterior end and an opposing first posterior end, the anterior and posterior ends defining a transverse midline therebetween; 2) a second member having a second joint surface, a second anterior end and an opposing second posterior end; and 3) a ball and socket joint between the fist and second joint surfaces and between the transverse midline and the first posterior end. The ball and socket joints permits relative rotation of the first and second member about a first axis parallel to the transverse midline and about a second axis perpendicular to the first axis. Additionally, at least one of the first and second joint surfaces is inclined away from the ball and socket joint entirely around the joint, and the other one of the first and second joint surfaces lies along a plane substantially parallel to both the first and second axes.

U.S. Pat. No. 5,676,701 to Yuan et al. discloses a low wear artificial spinal disc comprising: 1) a first component including a recess having a contoured surface with a 360° circumference; and 2) a second component including a projection having a contoured surface with a 360° circumference. The contoured surfaces permit unrestricted rotational motion and a flexion/extension bending motion between the components relative to a standing patient's spinal axis. The flexion/extension angle is between about 20°–30°.

A human spinal disc can be thought of as a gel filled sac which employs various modes of articulation that provide for changing the instant center of rotation of adjacent vertebral surfaces relative to one another and that permit lateral-to-lateral and anteroposterior translation of vertebrae relative to one another. An artificial spinal disc should be capable of articulating in a fashion similar to a human spinal disc. However, articulation in known spinal disc prostheses comprising two or more articulating components is generally limited to modes wherein the instant center of rotation of the components relative to one another does not change. This absence of a physiological movement in the instant center of rotation with flexion, is responsible for the translation of nonphysiological forces to the adjacent disc surfaces which is believed to accelerate the rate of disc degeneration and the need for subsequent or additional surgical intervention. Accordingly, there exists a need for an artificial spinal disc comprising plural components which disc provides for articulation wherein an instant center of rotation changes and which disc provides for translation of adjacent vertebrae relative to one another.

Known prosthetic spinal discs suffer disadvantages including the movement of the end plates, dislocation of the endplates, polyethylene cold flow, cold-welds of metal on metal components, ossification of the annulus, and particulate wear and debris of the component parts. There remains a need for an artificial disc, which mimics natural spinal segmental motion and provides an improved alternative to spinal fusion. Analogous to the situation with degenerative hips and knees where viable mechanical substitutes exist to enhance function and relieve pain, such a device will relieve pain for patients with end-stage disc disease, promote the preservation of natural motion, and create a device with the durability necessary for long-term use. There remains a need for a prosthetic disc which can mimic natural segmental spinal motion, relieve pain, and provide durability for long-term use.

SUMMARY OF THE INVENTION

The present invention overcomes the disadvantages of known prosthetic spinal discs and thus is generally directed to a versatile artificial spinal disc which can be used to replace degenerated and massively ruptured discs of the lumbar spine. The construction of the present artificial disc is such that it can be easily implanted in the spine through an anterior or anteriolateral fashion. The present device is adapted to articulate in a manner resembling a human knee. The present spinal disc employs a mode of articulation wherein the instant center of rotation of its articulating surfaces changes during articulation. The articulating surfaces of the present device preferably have a construction similar to that of the articulating joint surfaces of a knee.

In one aspect, the invention provides an artificial spinal disc which articulates in a manner resembling a human knee, said disc comprising:

a first plate having a first outer periphery, a substantially flat first superior surface, an articulating bimodal convex-shaped first inferior surface, a first anterior end, a first posterior end, a first lateral side and a second lateral side; and a second plate having a second outer periphery, a substantially flat second inferior surface, an articulating bimodal concave-shaped second superior surface, a second anterior end, a second posterior end, a third lateral side and a fourth lateral side;

wherein:

said first and second plates articulate in a manner resembling a human knee when said first inferior surface, said first anterior end and said first posterior end are juxtaposed said second superior surface, said second anterior end and said second posterior end, respectively.

Another aspect of the invention provides an artificial spinal disc which has a changing instant center of rotation during anteroposterior flexion, said disc comprising:

a first plate having a first outer periphery, a first superior surface, an articulating bicondylar first inferior surface, a first anterior end, a first posterior end, a first lateral side and a second lateral side; and a second plate having a second outer periphery, a second inferior surface, an articulating bimodal concave-shaped second superior surface, a second anterior end, a second posterior end, a third lateral side and a fourth lateral side;

wherein:

first and second condyles of said bicondylar first inferior surface are juxtaposed in a lateral-to-lateral fashion;

first and second concave-shaped modes of said bimodal second superior surface are juxtaposed in a lateral-to-lateral fashion; and an instant center of rotation of said disc changes during anteroposterior articulation of said first and second plates.

In one embodiment, the articulating bicondylar first inferior surface comprises a structure wherein the configuration of each condyle is substantially similar, and a portion of the radius of curvature of each condyle, when viewed along a sagittal section at the midpoint of the condyle, is changing and can be described by a Fibonacci mathematical series. Due to the changing radius of curvature, flexion of this device in anteroposterior fashion provides for an anteroposterior translation or change in the disposition of an the instant center of rotation of the spinal disk.

The articulating surfaces of the first and second plates can have different arcs of curvature. At least one condyle of the bicondylar first inferior surface of the first plate can have an arc of curvature, along a sagittal section at the midpoint of the condyle, that approximates or is greater than the arc of curvature of a respective concave-shaped mode of the second plate.

The first and second concave-shaped modes can have a larger radius of curvature along a sagittal section at their respective midpoints than their respective first and second condyles have along a sagittal section of their respective midpoints. Accordingly, the first and second concave-shaped modes can be smaller, or shallow, in vertical depth than their respective first and second condyles are in vertical height.

The articulating surfaces of the artificial spinal disc can be adapted to permit translation, in a lateral-to-lateral fashion, of the instant center of rotation during sideward leaning or tilting, i.e., bending of the spine from side to side. Accordingly, the juxtaposed first and second concave-shaped modes can form a channel which permits lateral-to-lateral translation of the bicondylar surface during articulation.

The lateral sagittal sections of each condyle can be substantially similar and can be adapted to provide a gentle braking to the rotation of the plates with respect to one another about a vertical axis.

The first and second concave-shaped modes of the articulating second superior surface can be separated by a raised surface interposed the first and second modes. The raised surface can provide a gentle braking of the side-to-side translation of the plates with respect to one another.

The first superior surface and the second inferior surface are adapted to be placed between adjacent inferior and superior surfaces of adjacent vertebrae. The first superior and second inferior surfaces can be substantially flat, or planar, in either one or both a lateral-to-lateral direction or an anteroposterior direction. The artificial spinal disc can further comprise one or more attachment means to facilitate attaching the device to the adjacent vertebrae. The outer peripheries of the plates can be kidney-shaped.

In another aspect, the present invention provides a method for replacing a spinal disc in a human spine comprising the steps of:

removing a spinal disc from a human spine to provide an intervertebral space defined by a superior vertebra and an inferior vertebra;

inserting an articulating artificial spinal disc in said intervertebral space; and attaching said artificial spinal disc to said superior and inferior vertebrae;

wherein the artificial spinal disc is as described herein.

The method of the invention can include the additional step of adapting a surface of vertebra adjacent the artificial spinal disc such that the vertebral surfaces will be substantially complementary to the flat surfaces of the artificial spinal disc. In a preferred embodiment, the step of inserting the artificial spinal disc will be conducted such that the artificial spinal disc is inserted from an anterior or anteriolateral direction.

Other features, advantages and embodiments of the invention will be apparent to those skilled in the art by the following description, accompanying examples and appended claims.

BRIEF DESCRIPTION OF THE DRAWINGS

The following drawings are part of the present specification and are included to further demonstrate certain aspects of the invention. The invention may be better understood by reference to one or more of these drawings in combination with the detailed description of the specific embodiments presented herein.

FIG. 1b is a rear or posterior elevation view of the first plate of the spinal disc of FIG. 1a.

FIG. 1c is a bottom or inferior plan view of the first plate in FIG. 1a.

FIG. 2b is a rear or posterior elevation view of a second disc of FIG. 2a.

FIG. 2c is a top or superior plan view of the second plate of FIG. 2a.

FIGS. 5a–5d are side elevation views of various different embodiments of the second plate according to the invention.

FIG. 6a is a bottom plan view of the flat inferior surface of the second disc according to the invention.

FIG. 6b is a sectional side elevation view along lines 6b—6b of the second plate depicted in FIG. 6a.

DETAILED DESCRIPTION OF THE INVENTION

Referring now to FIGS. 1a–1c and 2a–2c, the artificial spinal disc of the invention is used as a substitute for a chronically degenerated, painful and/or ruptured and excised human intervertebral disc. The artificial spinal disc is essentially a kidney-shaped device, as viewed from a top plan view, comprising first (1) and second (10) kidney-shaped plates which can be placed between adjacent vertebrae (not shown) in a spine. Each of the first (1) and second (10) plates has an anterior end ($A_1$ and $A_{10}$, respectively), an opposing posterior end ($PS_1$ and $PS_{10}$, respectively), and two lateral sides ($L_1$, $L_2$ and $L_{10}$, $L_{12}$, respectively).

The first (1) and second (10) plates articulate with one another to form a human knee-type joint that permits limited rotation of the first (1) and second (10) plates relative to one another about a vertical axis ($X_1$). This limitation of rotation is within a physiologic range, i.e., from 0°–10° of rotation or +/−5 degrees off center in either direction, to provide moderate degrees of restraint to the device. The first plate (1) further comprises a substantially planar, or flat, first superior surface (2) and an opposing contoured or articulating first inferior surface (3) comprising two laterally juxtaposed convex portions (4, 5) of substantially the same shape. The second plate (10) further comprises a substantially planar, or flat, second inferior surface (11) and an opposing contoured or articulating second superior surface (12) comprising two laterally juxtaposed concave portions (13, 14) which are larger in size than the respective convex portions of the first plate (1).

The first (1) and second (10) plates can be described by the frontal (or transverse) and median (or sagittal) sections of their respective articulating surfaces. The articulating first inferior surface (3) of the first plate (1) has a sagittal section, in the anterior to posterior direction along plane $P_1$, resembling an outwardly curved arch, i.e. convex, having a varying radius of curvature. The condyles (4, 5) can each have a sagittal section, along the midpoint of each condyle (see the planes $P_4$ and $P_5$, respectively), resembling a curve comprising at least a portion having a varying radius of curvature. In a preferred embodiment, the shape of the curve in the sagittal section will approximate the shape of a curve described by a Fibonacci mathematical series.

Figure 1A:
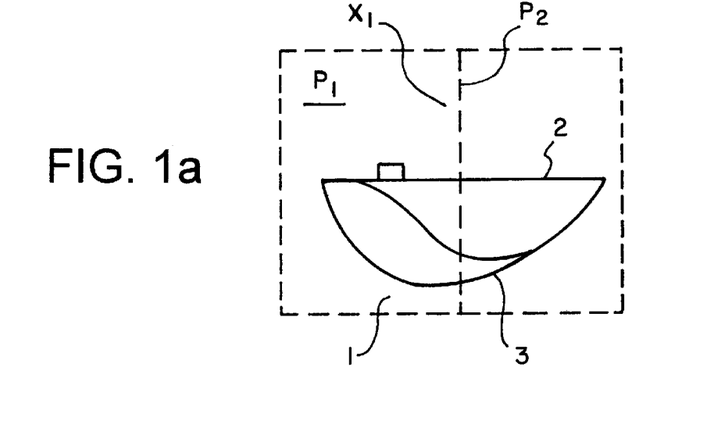
FIG. 1a is a side elevation view of the first plates of the artificial spinal disc according to the invention.
Figure 1B:
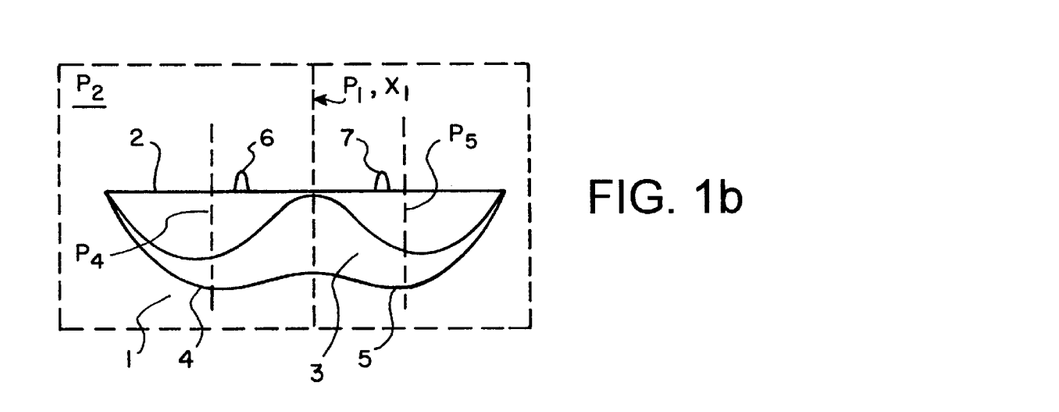
Figure 1C:
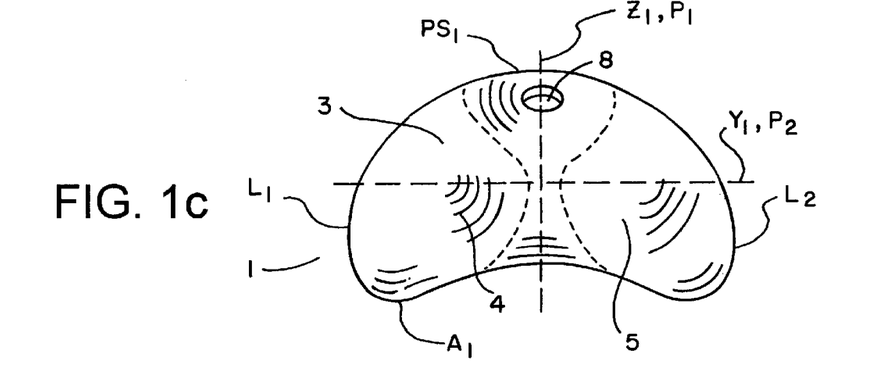

The condyles (4, 5) can have a combined transverse section, in a lateral to lateral direction along plane $P_2$, resembling a bimodal outwardly curved arch, i.e. two convex curves, having a varying radius of curvature. The plane $P_2$ is disposed approximately half way between the anterior ($A_1$) and posterior ($PS_1$) ends. The condyles (4, 5) can each have an individual transverse section, along plane $P_2$, resembling a curve comprising at least a portion having a varying radius of curvature. In a preferred embodiment, the shape of the curve of the transverse section for each condyle (4,5) will approximate the shape of a curve described by a Fibonacci mathematical series.

Figure 2A:
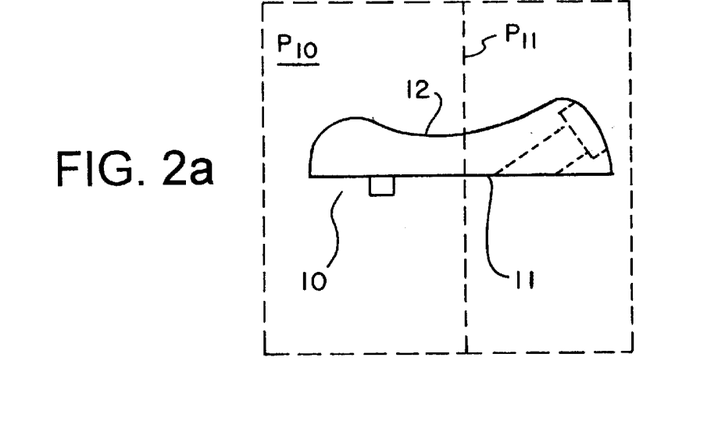
FIG. 2a is a side or lateral elevation view of the second plate of the spinal disc according to the invention.
Figure 2B:
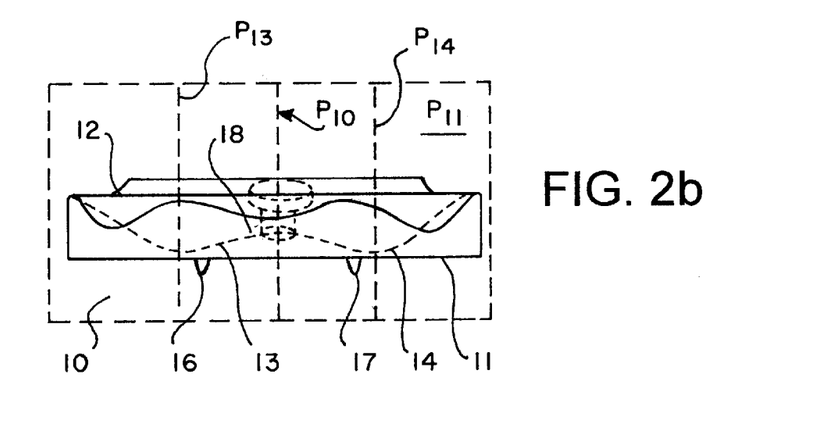
Figure 2C:
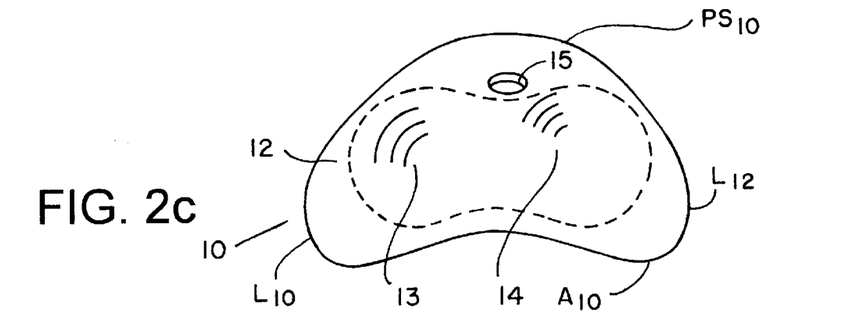

The articulating second superior surface (12) of the second plate (10) has a sagittal section, in an anterior to posterior direction along plane $P_{10}$, resembling an inwardly curved arch, i.e., concave, having a varying radius of curvature. The modes (13, 14) can each have a sagittal section, along the midpoint of each mode (see the planes $P_{13}$ and $P_{14}$, respectively), resembling a curve comprising at least a portion having a varying radius of curvature. In a preferred embodiment, the shape of the concave curves in the sagittal section will approximate the shape of a curve described by a Fibonacci mathematical series.

The concave modes (13, 14) can have a combined transverse section, in a lateral to lateral direction along plane $P_{11}$, resembling a bimodal inwardly curved arch, i.e. two concave curves. The plane $P_{11}$ is disposed approximately half way between the anterior ($A_{10}$) and posterior ($PS_{10}$) ends. The concave modes (13, 14) can each have an individual transverse section, along plane $P_{11}$, resembling a curve comprising at least a portion having a varying radius of curvature. In a preferred embodiment, the shape of the curve of the transverse section for each concave mode (13, 14) will approximate the shape of a curve described by a Fibonacci mathematical series.

The respective shapes of the concave and convex portions of the articulating surfaces (3, 12), respectively, will comprise portions that are substantially complementary; however, the articulating surfaces will be shaped to permit articulation of the plates (1) and (10) in a manner resembling the articulation of a human knee. Thus, the articulating surfaces (3, 12) can be regularly or irregularly shaped as at least partially complementary portions of spheroids, paraboloids, hyperboloids or ellipsoids of revolution or combinations thereof As discussed above, the concave and convex portions of the articulating surfaces can be described by both coronal, i.e., transverse, and sagittal arcs which are variable, i.e., have varying radii of curvature, and allow for changing instant centers of rotation and moderate degrees of rotation during articulation of the surfaces (3, 12).

The articulating surfaces (3) and (12) are designed so that the respective concave and convex portions thereof comprise a major portion of substantially the entirety of the respective articulating surfaces (3) and (12). Thus, while the articulating surfaces are surrounded by respective surfaces defining the outer periphery of each of the respective plates (1) and (10), the articulating surfaces do not have respective inferior and superior surface portions that completely surround the articulating respective portions of said surfaces. For example, substantially all of the convex-shaped portions (4, 5) of the articulating surface (3) can articulate with substantially all of the cave-shaped portions (13, 14) of the articulating surface (12).

Figure 3A:
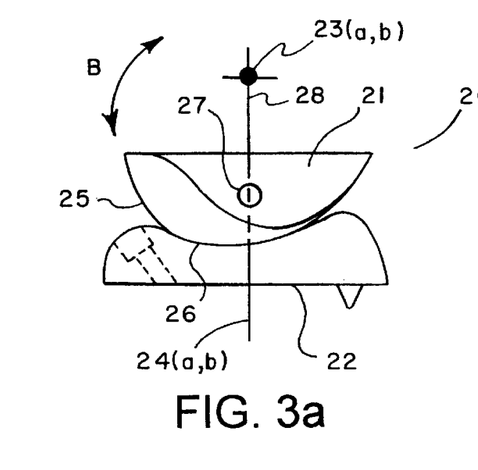
FIGS. 3a and 3b are side elevation views of the artificial spinal disc according to the invention wherein the first and second plates are depicted in two different stages of articulation.
Figure 3B:
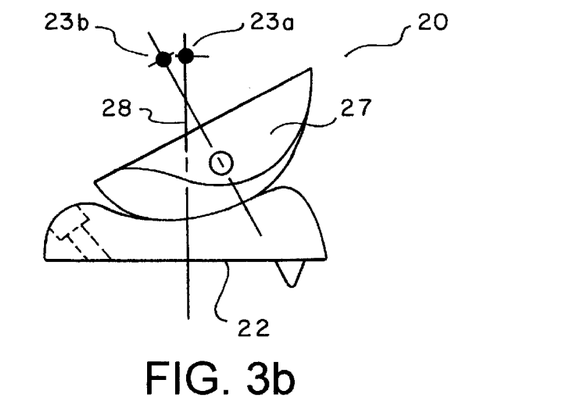

FIGS. 3a and 3b depict an artificial spinal disc (20) according to the invention comprising a superior first plate (21) and an inferior second plate (22). The first plate (21) comprises a first articular surface (25) which articulates with a second articular surface (26) of the second plate (22). Since FIG. 3a is a side elevation view of the artificial spinal disc (20), it corresponds to a lateral view of the device. Therefore, as the plates (21) and (22) articulate along their articulating surfaces (25) and (26), respectively, the first plate (21) will move in the direction indicated by the arrow (B) from the home position depicted in FIG. 3a to a second position depicted in FIG. 3b. In the home position, the plates (21 and 22) share a common center of rotation (23a, 23b); however, when the first plate (21) is articulated to a second position as depicted in FIG. 3b, the instant centers of rotation (23a, 23b) are no longer coincident. Therefore, when a patient using the present device bends in a forward or backward manner, i.e., flexes in an anteroposterior fashion, the instant centers of rotation (23a, 23b) will be displaced away from each other in an anteroposterior fashion, i.e., there will be an anteroposterior translation of the instant center of rotation (23b) with respect to the instant center of rotation (23a).

Figures 4A, 4B:
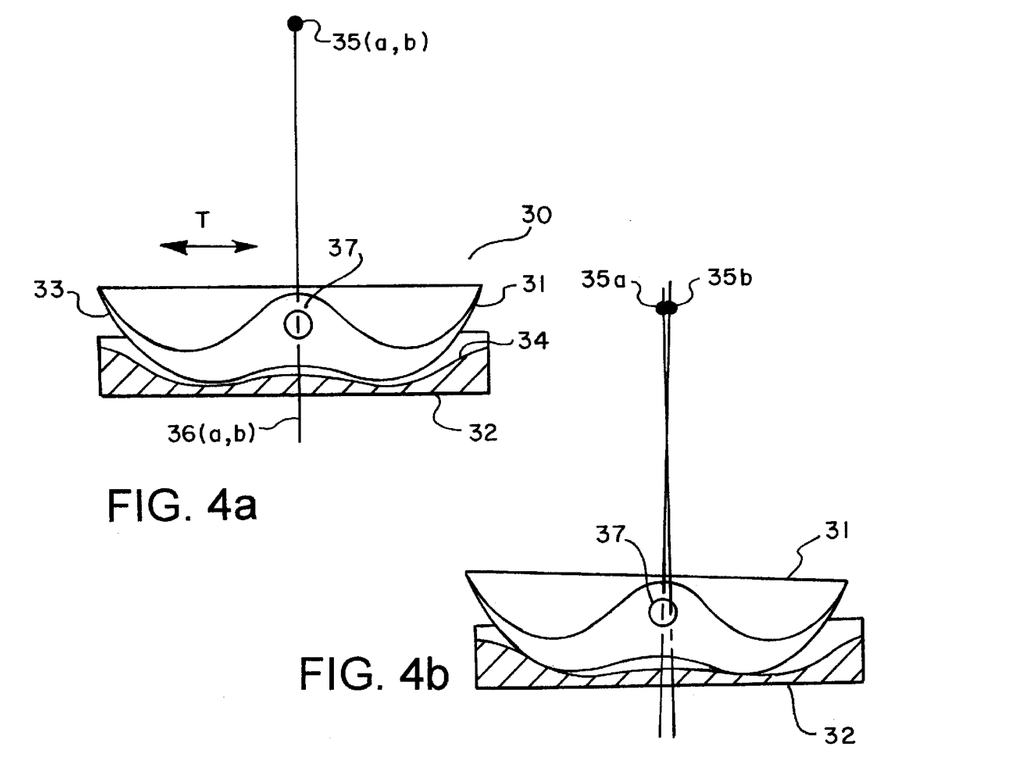
FIGS. 4a and 4b are partial cross-sectional rear elevation views of the artificial spinal disc according to the invention wherein the first and second plates are depicted in two different stages of articulation.

FIGS. 4a and 4b depict partial cross-sectional rear, or posterior, elevation views of an artificial spinal disc (30) comprising a first superior plate (31) and a second inferior plate (32). The first superior plate (31) comprises a bicondylar articulating surface which articulates with a bimodal concave articulating surface (34) of the second plate (32). The plates (31 and 32) are depicted in a home or neutral position; however, when the first plate (31) is translated laterally along the arrow (T) with respect to the second plate (32), the first plate (31) will tilt slightly with respect to the second plate (32) and the instant centers of rotation (35a, 35b) will be displaced from one another. Therefore, in one embodiment of the invention, the artificial spinal disc will comprise first and second articulating surfaces which are adapted to provide a changing center of rotation when the articulating surfaces are translated or articulated with respect to one another in a lateral-to-lateral fashion.

Figures 5A, 5B, 5C, 6A, 6B:
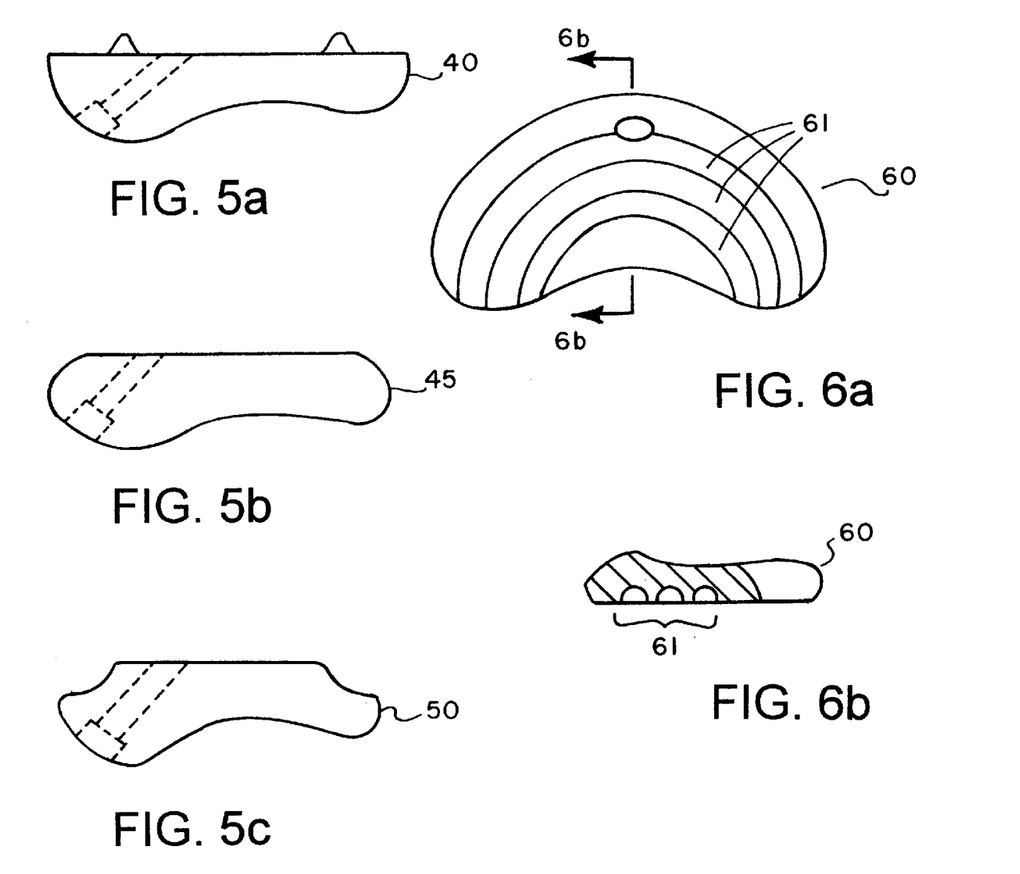
Figure 5D:
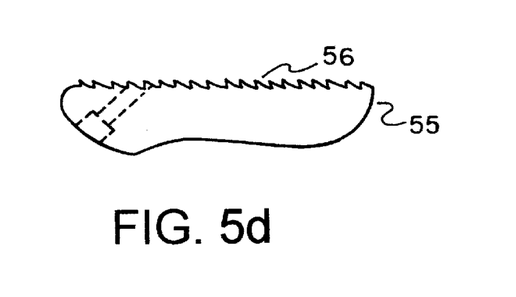

FIGS. 5a–5d depict four additional embodiments (40, 45, 50 and 55) of the second plate of the invention which comprises the bimodal concave shaped surface that engages with and articulates with a bicondylar or bimodal convex shaped surface of a first plate. The alternate embodiments of the vertebral end-plate, i.e., the second plate, depict various embodiments where the rim-bearing and weight-bearing capacities of the artificial spinal disc have been enhanced. They include embodiments comprising pegged and concave configurations as well as an embodiment (50) comprising a central weight-bearing and contoured element (FIG. 5c) having additional peripheral rim-bearing structure that will loadshare on it is periphery as well as in the cancellous centrum of a vertebra. FIG. 5d depicts an alternate embodiment (50) having a porous surface (56) for the ingrowth of bone, such as by the additional of hydroxyapetite, to enhance the adhesion of the spinal disc to an adjacent vertebra. The embodiment of FIG. 5d is also adapted to reduce the effect of the moment to cause anterior extrusion of the implant via an increase in the frictional forces that resist this vector. The embodiments of FIGS. 5a–5d also demonstrate the functional fixation provided by cancellous pitch and threaded fixation screws of various sizes, locations and directions that are envisioned to cause immediate fixation of the artificial spinal disc to adjacent vertebra and to prevent motion between the first and second plates of the artificial spinal disc.

FIG. 6a depicts a bottom plan view of a second plate (60) according to the invention wherein the flat inferior surface of the plate that contacts an adjacent vertebra comprises a plurality of grooves, channels or wells (61) which provide for a macro-textured surface that is designed to enhance the survival of the subcondral structure of the end plate while distributing load to the vertebra. The curved and radiating grooves can prevent the congestion of the microvasculature associated with complete coverage and occlusion of the end plates. FIG. 6b is a sectional side elevation view of the second plate (60) of FIG. 6a.

Referring again to FIGS. 3a–3b, the plates (21 and 22) are adapted to articulate and rotate relative to one another about a lateral-to-lateral, or transverse, axis during anteroposterior flexion along the arrow (B). Relative to the vertical axis (28), the first plate (21) is adapted to permit articulation in an anterior direction of up to about 15° from the neutral or home position shown in FIG. 3a and in a posterior direction of up to about −5° relative to the home position depicted in FIG. 3a.

Referring to FIGS. 4a and 4b, the artificial spinal disc (30) comprising a first plate (31) (shown in elevation) and a second plate (32) (shown in section) is adapted to permit articulation of the plates relative to one another about a median saggital axis which extends anteroposteriorly through the device. Specifically, when the first plate (31) is displaced laterally, or is translated laterally, in the direction of the arrow (T), the instant center of rotation (35a and 35b) will be displaced relative to one another and the first plate (31) will assume a tilted position relative to the first plate (32). Note that although the articulating surfaces (33 and 34) each comprise portions having a varying radius of curvature, the concave shaped sections of the articulating surface (34) each have a radius of curvature that is larger than a respective condyle portion of the articulating surface (33) with which it articulates. Accordingly, while each concave shaped mode of the bimodal articulating surface (34) can comprise curved portions described by a Fibonacci mathematical series, the corresponding convex shaped condyle of the articulating surface (33) will comprise curved portions which can be described by a second range of the Fibonacci mathematical series such that the radii of curvature of the convex shaped condyles will be smaller than the radii of curvature of the concave shaped modes. The degree of tilting of the first plate (31) relative to the second plate (32) will range from about 2–5° off center in either direction. In a preferred embodiment, the degree of tilting of the first plate (31) relative to the second plate (32) will range from 1–2.5°.

In preferred embodiments, the degree of anteroposterior flexion of the first plate (21) relative to the second plate (22) will range from about 3–15° in either direction, more preferably 1.5–7.5° in either direction, and more preferably will span 5–7°. In another preferred embodiment, the degree of anteroposterior flexion of the first plate (21) relative to the second plate (22) will have a maximum range of motion of about 10°, and more preferably about 5–7°. In yet another preferred embodiment, the average range of extension will be from 0 to −5° and more preferably from 0 to −3°. Still yet another preferred embodiment provides an average flexion of about −5 to 10° along the saggital plane. It will be understood by the artisan of ordinary skill that a negative degrees indicates an extension of the spinal disc and a positive degrees indicates a flexion of the spinal disc, where flexion refers to bending the spine in a forward or anterior direction.

Figure 7:
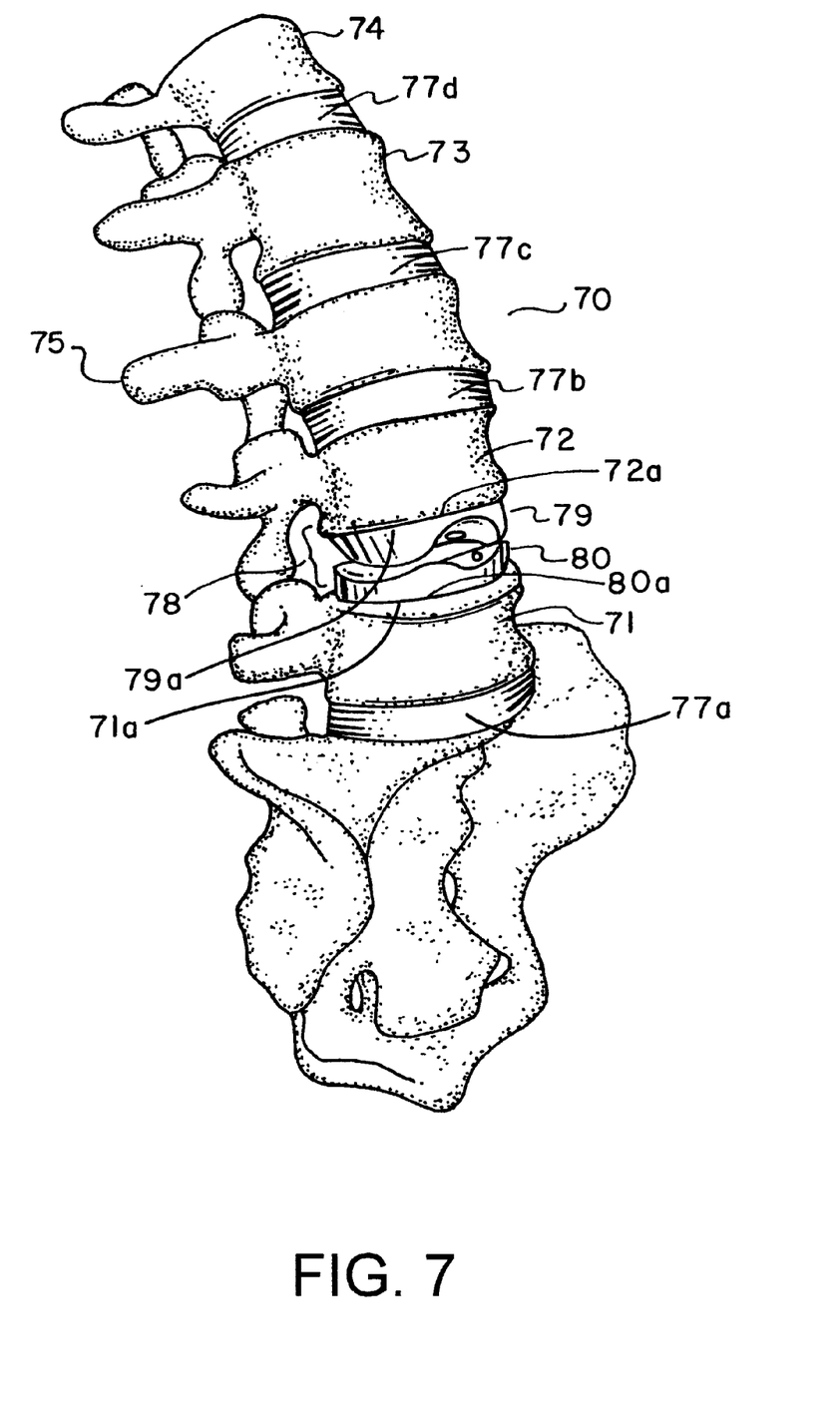

FIG. 7 depicts an artificial spinal disc (78) according to the invention implanted in a human spine (70) which comprises plural vertebrae (71, 72, 73, 74, 75) and plural interposed spinal discs (77a–77d). The artificial spinal disc (78) has a first plate (79) and a second plate (80) interposed the superior vertebra (72) and the inferior vertebra (71), respectively. The inferior surface (72a) of the superior vertebra (72) is depicted as planar, or flat, so as to optimize the substantially flat superior surface (79a) of the plate (79). The superior vertebral surface (71a) of the inferior vertebra (71) is also depicted as planar so as to optimize contact with the inferior surface (80a) of the plate (80). Although not shown, the plates (79 and 80) and consequently the vertebrae (72 and 71), respectively, are held adjacent one another by the musculature and other body tissues which normally surround the spinal column (70).

Each of the plates (1) and (10) can include attachment means which facilitate attachment of the artificial spinal disc to adjacent vertebrae. In the embodiment of FIGS. 1a–1c and 2a–2c, the attachment means comprises at least two projections (6, 7) and (16, 17) on each of the planar surfaces (2) and (11) of the plates (1) and (10), respectively. The projections (6, 7) mate with corresponding cavities (not shown) in adjacent vertebrae which are superior and inferior to the artificial spinal disc. Alternatively or additionally, the attachment means can also comprise multiple screw holes in the end of each plate (1, 10) through which are inserted respective cancerous screws that are then screwed into the adjacent vertebral body that are in contact with the artificial spinal disc. The attachment means according to the invention can comprise one or more known means for affixing or attaching solids to one another. By way of example and without limitation, attachment means can include a screw, nail, rivet, adhesive, wire, band, strap, and embodiments for porous coating of the prosthesis endplate screws or the combination and locking mechanisms to affix the screw to the intervertebral disc component.

The holes (8, 15), if present, can be shaped as desired. They can be adapted to receive and retain screws, nails, rivets, spikes and other articles used to secure the plates (1, 10, respectively) to adjacent vertebrae. For example, the holes (8, 15) can be countersunk or can have locking methods or mechanisms which stabilize the screw to the artificial intervertebral disc prosthesis.

Although FIGS. 1a–1b and 2a–22b depict the attachment means (6, 7 and 16, 17) on planar surfaces (2) and (11), respectively, as being disposed toward the anterior ends (A1) and (A10), respectively, the attachment means can be disposed anywhere within the artificial spinal disc. It will generally be necessary for each plate (1) and (10) to have at least one attachment means by which it is secured to an adjacent vertebra. The attachment means according to the invention can be shaped as desired in order to optimize performance in a particular use or environment. The attachment means can comprise plural similar or dissimilar attachment means. In a preferred embodiment, the attachment means will comprise two or more projections (6, 7) and (16, 17) on the planar surfaces (2) and (11), respectively for engagement with respective cavities or bores within adjacent inferior and superior surfaces of respective adjacent vertebrae. The planar surface can further comprise porous coatings to enhance ossication thereof such as by promoting the growth of bone therein. Osteoinductive, osteoconductive, osteogenic and other fusion enhancing materials are contemplated.

Although FIGS. 1c and 2c depict a particular embodiment of a kidney shape, the outer peripheries of the plates (1) and (10) of the artificial spinal disc can include embodiments wherein the anterior ($A_2$ and $A_{10}$), respectively, or posterior ($PS_1$ and $PS_{10}$), respectively, ends or the lateral sides (L1, L2) and (L10, L12), respectively, can have different or similar radii of curvature. The artificial spinal disc can be shaped additionally as a single condylar structure without limitation or need for an intercondylar notch to be integral in one part of the component.

Although the substantially planar first superior (2) and second inferior (11) surface are intended to be flat, they can have depressions, ridges, ribs, bosses, projections, indentation, dimples and the like.

The plates (1, 10) of the artificial spinal disc are generally intended to be rigid, semi-flexible or resilient and thus will comprise materials such as, by way of example and without limitation, metal, hard rubber, plastic, polymer, alloy, composite material, ceramic, ceramic metal alloy or combinations thereof.

The plates (1, 10) can be manufactured by a variety of methods including: casting, stereolithography, machining, plasma spraying, coating, polishing, or investment casting.

Although the plates (1, 10) are depicted as having lateral to lateral lengths greater than their respective anterior-to-posterior widths, the plates can be dimensioned as desired. Thus, the width of the plates (1, 10) can be greater than, equal to or less than the respective lengths. In most cases, the superior-to-inferior height of each of the plates (1, 10) will be less than both its width and length.

Proximal to the anterior border of the vertebral body in the posterior end will be adjacent to the posterior vertebral body but away from the underlying spinal nerves. Although, FIGS. 1a–1c and 2a–22c depict the first plate (1) as being the superior plate, the spinal disc of the invention can be flipped over so that the second plate (10) is the superior plate.

The articulating spinal disc prosthesis of the invention differs from known prostheses used for the replacement of knee joints in at least one of the following ways. The present artificial spinal disc is smaller in construction, has a smaller articulating bicondylar surface, provides only a limited range of articulation in flexion and extension and can be designed such that the changing instant center of rotation will occur in either an anterior or posterior direction along a saggital plane. In a preferred embodiment, the change in the instant center of rotation of the artificial spinal disc will occur in a manner opposite that occurring in a human knee.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

What is claimed is:

1. An artificial spinal disc which articulates, said disc comprising:

a first plate having a first outer periphery, a substantially flat first superior surface, a first inferior articulating surface, a first anterior end, a first posterior end, a first lateral side and a second lateral side; and a second plate having a second outer periphery, a substantially flat second inferior surface, a second superior articulating surface, a second anterior end, a second posterior end, a third lateral side and a fourth lateral side;

wherein:

said first and second plates can articulate in an anteroposterior fashion when said first inferior surface, said first anterior end and said first posterior end are juxtaposed said second superior surface, said second anterior end and said second posterior end, respectively;

at least one of said first inferior articulating surface and said second superior articulating surface comprises a changing anteroposterior arc of radius; and said disc has an instant center of rotation in flexion which moves in an anteroposterior direction during anteroposterior articulation of said disc.

2. The artificial spinal disc of claim 1, wherein said articulating first inferior and second superior surfaces have major portions which are substantially complementary.

3. The artificial spinal disc of claim 1, wherein said first and second outer peripheries are substantially kidney shaped.

4. The artificial spinal disc of claim 1, wherein at least one of said flat first superior and said flat second inferior surfaces comprises attachment means for securing said spinal disc to a vertebra.

5. The artificial spinal disc of claim 1, wherein said first plate is superior to said second plate.

6. The artificial spinal disc of claim 1, wherein said second plate is superior to said first plate.

7. The artificial spinal disc of claim 1, wherein at least one of said first and second plates includes a hole therethrough for use in securing said at least one plate to a vertebra.

8. The artificial spinal disc of claim 1, wherein a first mode of said bimodal convex-shaped first inferior surface is a substantial mirror image of a second mode of said bimodal convex-shaped first inferior surface.

9. The artificial spinal disc of claim 1, wherein a first mode of said bimodal concave-shaped second superior surface is a substantial mirror image of a second mode of said bimodal concave-shaped second superior surface.

10. The artificial spinal disc of claim 1, wherein the spinal disc has bilateral symmetry.

11. The artificial spinal disc of claim 1, wherein each of said first and second plates comprises at least one attachment means.

12. The artificial spinal disc of claim 1, wherein each of said first and second plates comprises two different attachment means.

13. The artificial spinal disc of claim 1, wherein each mode of said bimodal convex-shaped first inferior surface is disposed along a midline between said first anterior and said first posterior ends.

14. The artificial spinal disc of claim 1, wherein said first and second plates can translate in a lateral to lateral direction with respect to one another.

15. The artificial spinal disc of claim 1, wherein said first and second plates can rotate with respect to one another about a vertical axis.

16. The artificial spinal disc of claim 15, wherein said rotation is limited to being within a normal physiological range.

17. The artificial spinal disc of claim 1, wherein the instant center of rotation moves in an anterior direction during anteroposterior articulation of said disc.

18. The artificial spinal disc of claim 1, wherein the first inferior articulating surface is bimodal convex-shaped and the second superior articulating surface is bimodal concave-shaped.

19. The artificial spinal disc of claim 18, wherein the bimodal convex-shaped first inferior articulating surface comprises a bicondylar structure wherein each condyle has a changing anteroposterior arc of radius defined by a Fibonacci mathematical series.

20. The artificial spinal disc of claim 18, wherein:

said bimodal convex-shaped first inferior articulating surface comprises a bicondylar structure wherein each condyle comprises the same changing arc of radius.

21. The artificial spinal disc of claim 20, wherein said arc of radius describes a Fibonacci mathematical series.

22. The artificial spinal disc of claim 18, wherein each of said convex-shaped first inferior surface and said concave-shaped second superior surface are defined by variable coronal and sagittal arcs that permit said first and second plates to rotate relative to one another about a vertical axis in a limited fashion.

23. A method for replacing a spinal disc in a human spine comprising the steps of:

(a) removing a spinal disc from a human spine to provide an intervertebral space defined by a superior vertebra and an inferior vertebra;

(b) inserting an articulating artificial spinal disc according to claim 1 in said intervertebral space; and (c) attaching said artificial spinal disc to said superior and inferior vertebrae.

24. The method of claim 23 wherein said artificial spinal disc is inserted into said intervertebral space from one of an anterior and anteriolateral direction.

25. The method of claim 23 further comprising the following step before step (b):

(a') adapting a surface of each vertebra to be substantially complementary to said flat first superior and flat second inferior surface.

* * * * *

UNITED STATES PATENT AND TRADEMARK OFFICE
CERTIFICATE OF CORRECTION

PATENT NO.: 6,039,763

DATED: March 21, 2000

INVENTOR: Alexis P. Shelokov

It is certified that error appears in the above-identified patent and that said Letters Patent are hereby corrected as shown below:

Column 7, line 61, change "(50)" to -- (55) --.

Column 9, line 47, change "2a-22b" to -- 2a-2b --.

Column 10, line 34, change "2a-22c" to -- 2a-2c --.

Signed and Sealed this

Twenty-fourth Day of April, 2001

*Attest:*

NICHOLAS P. GODICI

*Attesting Officer*  *Acting Director of the United States Patent and Trademark Office*